(12) United States Patent
Kucklick

(10) Patent No.: US 12,185,941 B2
(45) Date of Patent: Jan. 7, 2025

(54) ARTHROSCOPIC CANNULA AND SUTURE MANAGEMENT SYSTEM

(71) Applicant: Cannuflow, Inc., Scotts Valley, CA (US)

(72) Inventor: Theodore R. Kucklick, Scotts Valley, CA (US)

(73) Assignee: Cannuflow, Inc., Scotts Valley, CA (US)

(*) Notice: Subject to any disclaimer, the term of this patent is extended or adjusted under 35 U.S.C. 154(b) by 0 days.

(21) Appl. No.: 18/415,822

(22) Filed: Jan. 18, 2024

(65) Prior Publication Data

US 2024/0156450 A1    May 16, 2024

Related U.S. Application Data

(63) Continuation of application No. 17/143,075, filed on Jan. 6, 2021, now Pat. No. 11,896,213, which is a continuation-in-part of application No. PCT/US2020/041210, filed on Jul. 8, 2020.

(60) Provisional application No. 62/871,621, filed on Jul. 8, 2019.

(51) Int. Cl.
*A61B 17/04* (2006.01)
*A61B 17/34* (2006.01)
*A61M 39/02* (2006.01)

(52) U.S. Cl.
CPC ...... *A61B 17/0469* (2013.01); *A61B 17/3421* (2013.01); *A61B 17/3423* (2013.01); *A61B 2017/0479* (2013.01); *A61B 2017/3488* (2013.01); *A61M 2039/0291* (2013.01)

(58) Field of Classification Search
CPC ............ A61B 17/0469; A61B 17/3421; A61B 17/3423; A61B 2017/349; A61B 17/06061; A61B 2017/3492
See application file for complete search history.

(56) References Cited

U.S. PATENT DOCUMENTS

| 10,357,282 B2 * | 7/2019 | Spenciner .......... A61B 17/3421 |
| 2008/0108875 A1 | 5/2008 | Kunkel |
| 2016/0354113 A1 | 12/2016 | Spenciner |

FOREIGN PATENT DOCUMENTS

| JP | 2010522626 | 7/2010 |
| JP | 2016513501 | 5/2016 |

OTHER PUBLICATIONS

Notification of Reasons for Refusal dated Jan. 9, 2024 from Japanese Patent Application No. 2022-500062.
Office Action dated Jun. 18, 2024 from U.S. Appl. No. 18/347,224.

* cited by examiner

*Primary Examiner* — Julian W Woo
(74) *Attorney, Agent, or Firm* — Crockett & Crockett, PC; K. David Crockett, Esq.; Niky Economy Syrengelas, Esq.

(57) ABSTRACT

A flexible portal cannula for use in arthroscopic surgery. Distally positioned flaps extend radially outwardly from the outer surface of the cannula and are resiliently foldable to lie against the outer surface of the cannula during insertion into a surgical portal, and resiliently biased to return to the radially outwardly extending position when unconstrained. Slots disposed around the perimeter of the flaps for anchoring and sorting sutures.

1 Claim, 11 Drawing Sheets

ARTHROSCOPIC CANNULA AND SUTURE MANAGEMENT SYSTEM

This application is a continuation of U.S. application Ser. No. 17/143,075, filed Jan. 6, 2021, which is a continuation-in-part of PCT Application PCT/US2020/041210, filed Jul. 8, 2020, which claims priority to U.S. Provisional Patent Application 62/871,621 filed Jul. 8, 2019.

FIELD OF THE INVENTIONS

The inventions described below relate to the field of arthroscopic surgery and more specifically, to portal access and suture management during arthroscopic surgery.

BACKGROUND OF THE INVENTIONS

Arthroscopy is a minimally invasive procedure for treating joint pathology and is a superior alternative to open joint arthrotomy. Arthroscopy has the advantage of less disruption to the joint tissues, and potentially faster healing. The scope of joints and pathologies that can be treated with arthroscopy has grown dramatically, and now includes hip, spine, and small joint procedures in addition to the traditional knee and shoulder procedures. However, arthroscopy remains a technically demanding procedure, and new instrumentation and procedures are constantly being developed.

Access to difficult to reach parts of the joint remains a significant challenge. While curved and flexible instruments are available to access these hard to reach areas of the joint, access portal devices have not kept up with the instrument advances. Some attempts have been made to develop flexible portals, however these have significant drawbacks either in being only slightly flexible, being very difficult to use, or being incompatible with standard portal placement techniques and instrumentation. For example, the Arthrex® PassPort Button Cannula™ is a rubbery cannula that provides instrument mobility in shoulder operations. However, delivery of the device is non-standard, requiring the surgeon to fold the device in half with a hemostat before insertion. What is needed is an instrument system that allows a high level of flexibility, high instrument mobility, and high ease of use while retaining compatibility with standard cannula placement techniques involving switching sticks and guide wires.

Suture management is also a challenge in these procedures. In procedures where pairs of sutures are used in common double loaded suture anchors, it is possible that the surgeon may tie the wrong pairs of sutures together, which can require significant extra surgical time and cost, as well as additional risk and trauma to the patient to correct. Suture management within the surgical site is desirable.

SUMMARY

The systems described below provide for insertion of a flexible portal cannula into a surgical portal, providing better retention of the cannula within the surgical portal. Distally positioned flanges, tabs or flaps extend radially outwardly from the outer surface of the cannula and are resiliently foldable to lie against the outer surface of the cannula during insertion into an incision, and resiliently biased to return to the radially outwardly extending position when unconstrained. Once the cannula is inserted into the workspace, a clip disposed on the cannula outer surface outside of the arthroscopic workspace acts to clamp tissue disposed between the clip and the flaps. Ridges on the shaft of the cannula allow for incremental adjustment of the level at which the clip may be secured to effect compression of tissue between the flaps and the clip. The clip can easily be frictionally engaged to the cannula after insertion to the desired compression.

The cannula clip also features a suture sorter for easier suture management. The clip has pairs of slots to sort and engage pairs of sutures used in common "double loaded" suture anchors until the sutures are used. These slots may be identified with markings, letters or numbers that associate the location and orientation of the slots to anatomical locations in the joint.

Suture management is also achieved through slots disposed on the perimeter of the cannula flaps and also on the cannula distal tip to facilitate suture management at the surgical site.

DETAILED DESCRIPTION OF THE INVENTIONS

Figure 1:
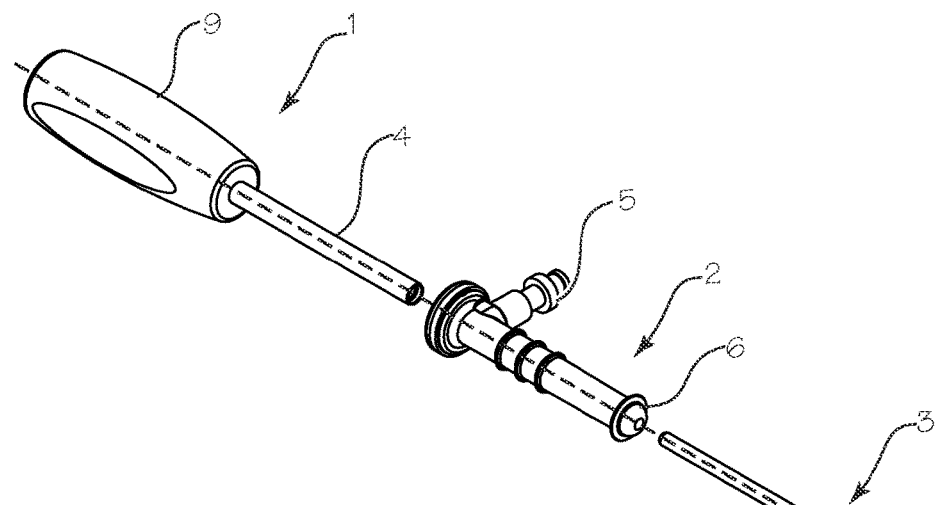
FIG. 1 illustrates an elastomeric portal cannula and driver system with paired engagement features.
Figure 3:
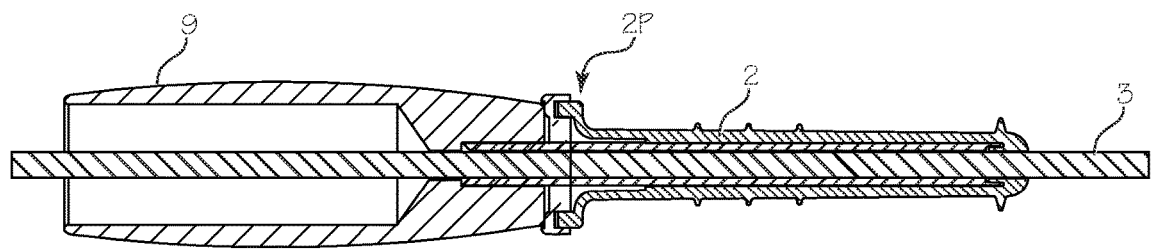
FIG. 3 illustrates the system of FIGS. 1 and 2 with a switching stick disposed within a lumen of a cannulated driver.
Figure 4:
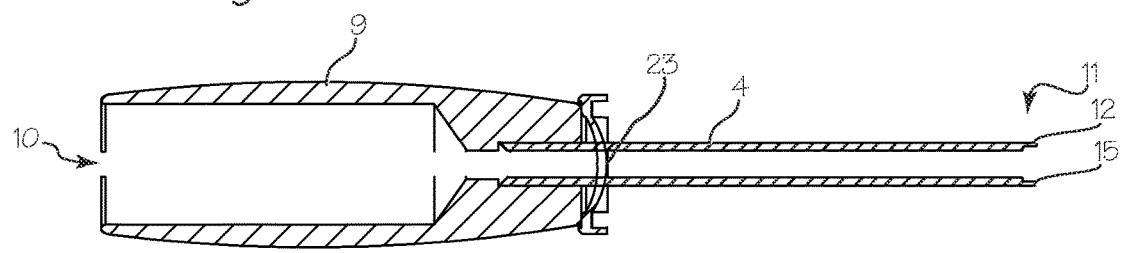
FIG. 4 illustrates the cannulated driver.
Figure 5:
FIG. 5 illustrates the switching stick.

FIG. 1 illustrates an exploded view of the system for driving a cannula into a surgical site. The system includes a rigid driver 1, a cannula 2, and a switching stick 3. The driver, as shown in FIGS. 3 and 4, comprises a handle 9 attached to the rigid tube 4. The driver may have a hemispherical seal 23. The driver may be cannulated (as shown) through its core to allow for insertion of the switching stick (FIG. 5). The cannula is delivered into place with the rigid tube 4 that has an interlocking feature at the distal tip that engages with a mating locking feature in the distal tip of the cannula. In this way, the proximal portion of the cannula is "pulled" into a surgical portal or incision from its distal tip as the distal tip is pushed. The system allows for the use of a switching 3, a rod typically about 4 mm in diameter that is used as a guide wire to place a cannula into a surgical portal. It should be appreciated that the switching stick is an optional feature, as is the driver cannulation which accommodates the switching stick.

Figure 2:
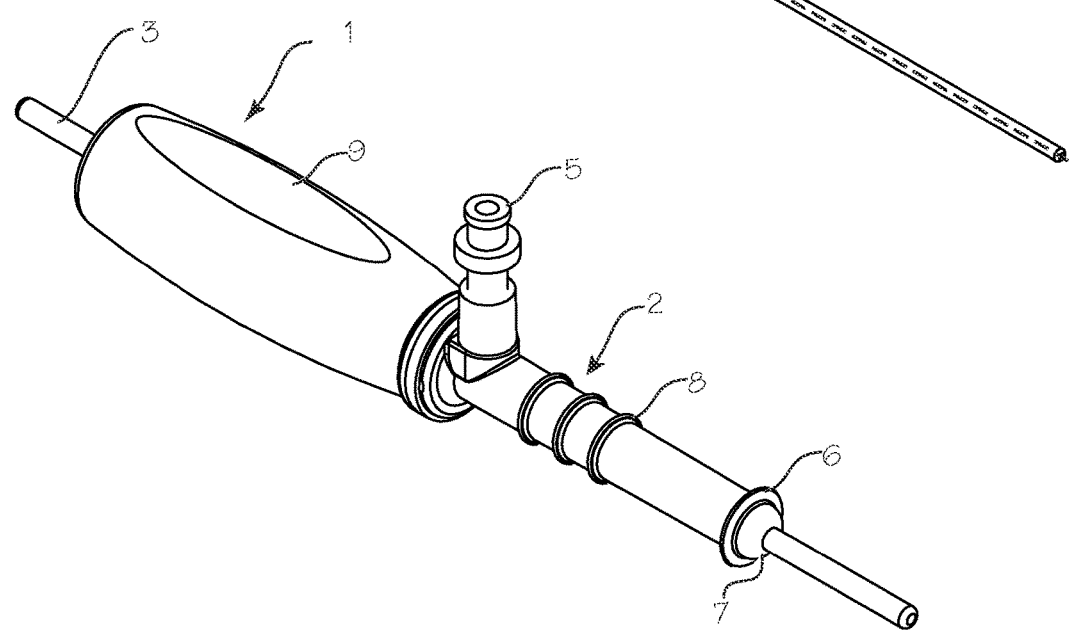
FIG. 2 illustrates the system of FIG. 1 with the driver disposed within the elastomeric portal cannula.

FIG. 2 illustrates the system of FIG. 1 when assembled, with the cannula disposed over the rigid tube 4. The cannula shown has a side port 5 to allow fluid inflow and outflow from the joint, providing fluid management in order to maintain clarity in the joint during the arthroscopic surgical procedure. The cannula has a flexible distal flange 6 or flap to retain the cannula in the joint, preventing it from backing out of the surgical site. An expandable distal wiper seal 7 may be provided to hold fluid in the joint and prevent fluid leakage. External retention ridges 8 are disposed over the exterior of the cannula.

In use, the driver is inserted into the proximal end 2P of the cannula 2 until the distally extending protrusion 12 at the distal tip 11 of the rigid driver engages the mating locking feature in the cannula. When the driver is engaged, the cannula is supported by the rigid tube. The switching stick 3 is inserted through the proximal end 10 of the driver 1, through the driver, and out the distal end of the driver and through the cannula. The entire assembly comprising the switching stick, rigid driver and cannula are inserted into the surgical portal or incision. When the cannula is in the desired position in the surgical site, the switching stick 3 is withdrawn, and then the rigid driver 1 is withdrawn.

Figure 6:
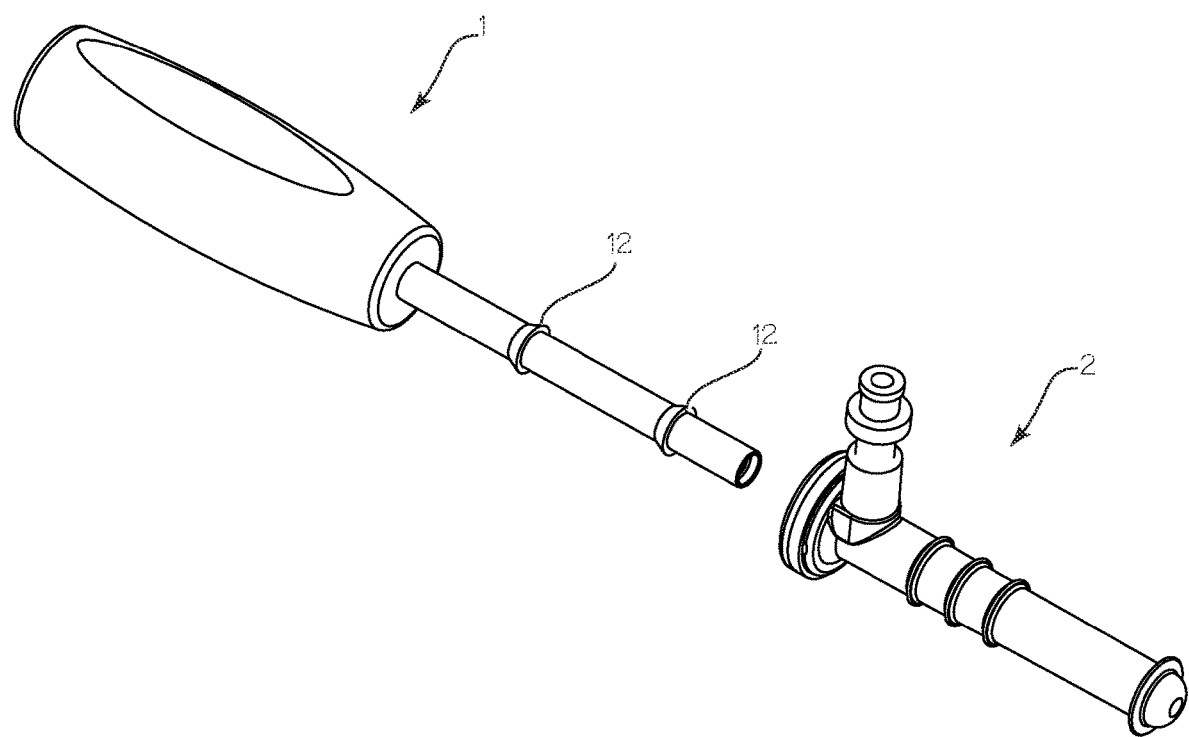
FIG. 6 illustrates an exploded view of a portal cannula and driver system having a plurality of gripping features.
Figure 7:
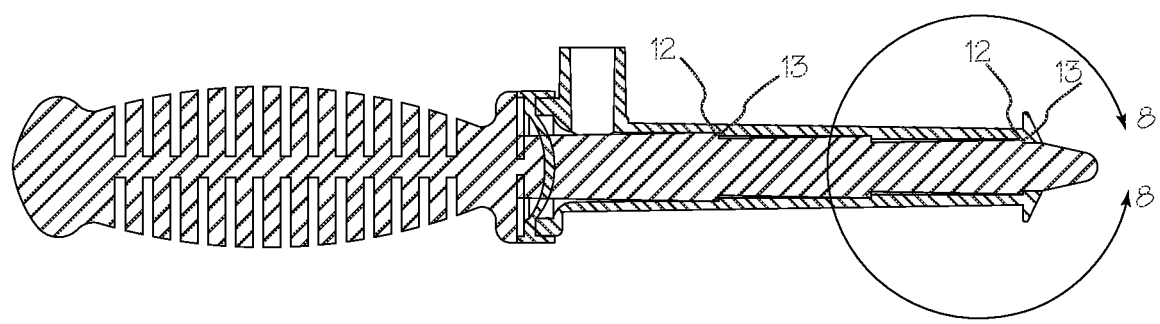
FIG. 7 illustrates the system utilizing a plurality of cylindrical gripping features.
Figure 8:
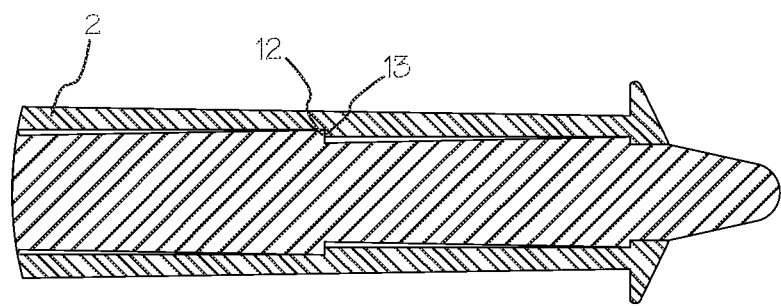
FIG. 8 illustrates the mating engagement between the plurality of cylindrical gripping features and the cannula of FIG. 7.

The driver and cannula can have a plurality of engaging features, as shown in FIGS. 6, 7 and 8. Each of the driver gripping features 12 correspondingly mate with detents 13 disposed on the inside wall of the cannula. Rather than one engagement point at the distal tip, the engagement features may be distributed along the length of the cannula. The plurality of engagement features allow the driver to push longer and lower durometer flexible cannulas into a surgical portal. The driver may have a uniform diameter. The gripping feature 12 of the driver engages with a proximally facing shoulder 13 of the cannula as shown in FIGS. 7 and 8.

Generally, the cannula is a flexible portal cannula for use in conjunction with the cannula driver. The cannula driver comprises a shaft having a distal end and a proximal end and at least one distally extending projection extending from its distal end, or extending distally from the outer surface of the driver proximate its distal end. The flexible portal cannula comprises a flexible tube, characterized by a proximal end and a distal end and a lumen extending from the proximal end to the distal end of the flexible tube, and a distal tip on the distal end. The distal tip of the flexible tube is adapted for insertion through a surgical portal into an arthroscopic workspace proximate a joint in a patient. The flexible tube has a proximally facing groove disposed on an inner surface thereof, proximate its distal end, which is sized and dimensioned to receive a distally extending projection of the cannula driver. The proximally facing groove can be an annular groove entirely circumscribing the inner diameter of the portal cannula, or it may extend merely partially around the inner diameter. As illustrated, the groove is most conveniently formed by a ring extending proximally within the distal tip of the portal cannula. The ring can be suspended or fixed to an inwardly protruding flange which protrudes inwardly from the inner wall of the portal cannula, but can also be fixed directly to, or depend directly from, the inner wall of the portal cannula. The driver may be a solid shaft, but is preferably hollow, with a lumen suitable for passage of a switching stick. Also, the driver may be split longitudinally, into two or more elongate sections, to be used in conjunction with a portal cannula having two or more lumens separated by longitudinally extending webs, where the webs are sized to fit in the space separating the elongate sections, to provide a system for inserting a multi-lumen portal cannula.

Figure 9:
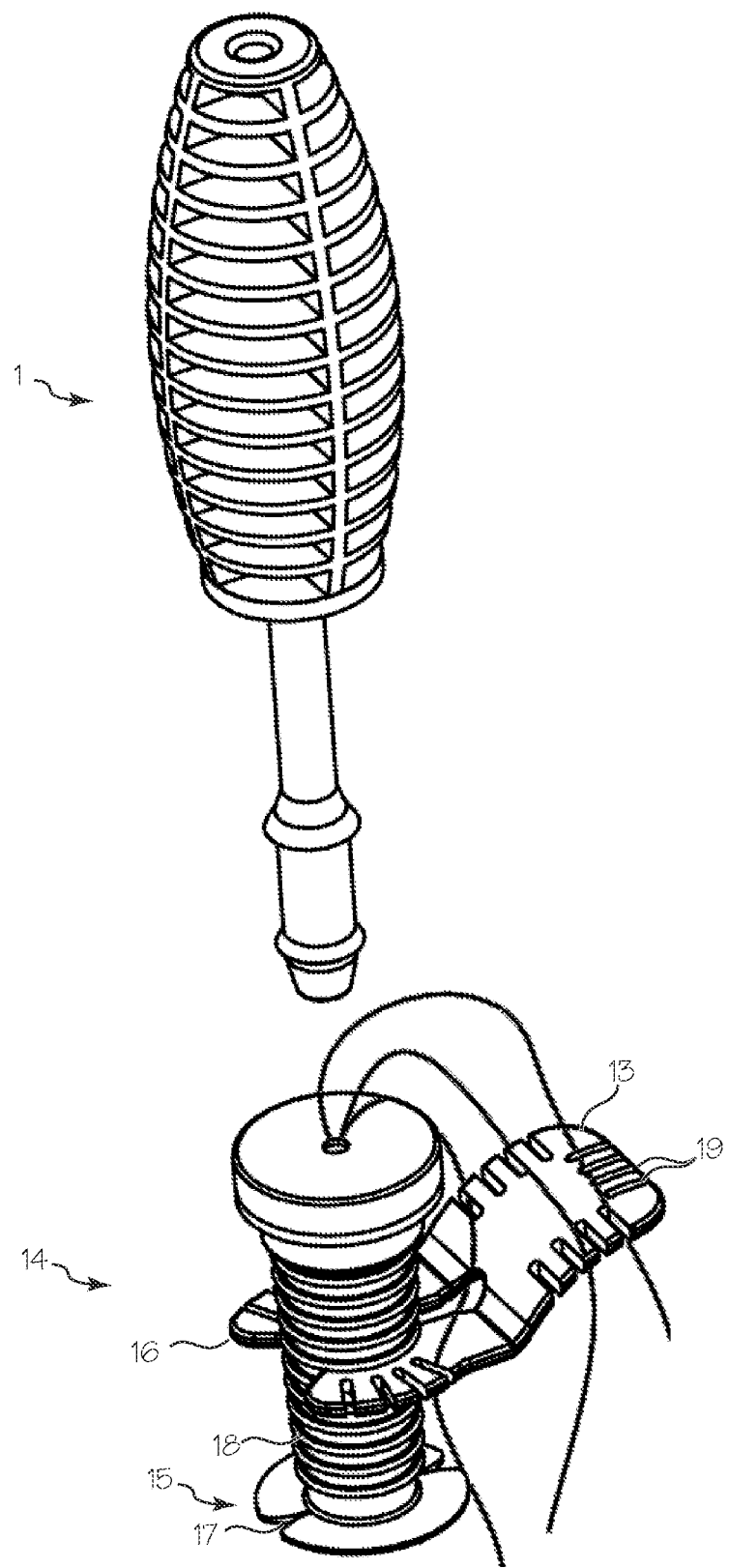
FIG. 9 illustrates a cannula with a distal flange and a clip with suture sorting.

FIG. 9 illustrates a cannula 14 with a distal flange 15 and a clip 16. The flange 15 is resiliently foldable in a proximal direction while the cannula is passed through the surgical incision, and resiliently biased to return to the radially outwardly extending position after passing through the incision and into the arthroscopic workspace. The combination of the distal flange 15 and the clip 16 is operable to clamp the tissue disposed between the clip and the flange. The distal flange 15 is disposed at the distal end of the cannula and may have one or more slits 17 that allow the flange to fold back and thus reduce the force needed to push the cannula into the workspace. Perforations at the base of the flange where the flange connects to the outer surface of the cannula may be provided for ease of folding. Alternatively, the flange with split arrangement can be characterized as separate flaps attached to the outer surface of the cannula as shown. Ridges 18 on the shaft of the cannula allow for incremental adjustment of compression applied by the clip. The clip 16 is configured to frictionally engage the cannula and can easily be slipped onto the cannula after insertion to the desired compression. The clip 16 can be positioned, relative to the flange 15, to compress intervening tissue.

Figure 10:
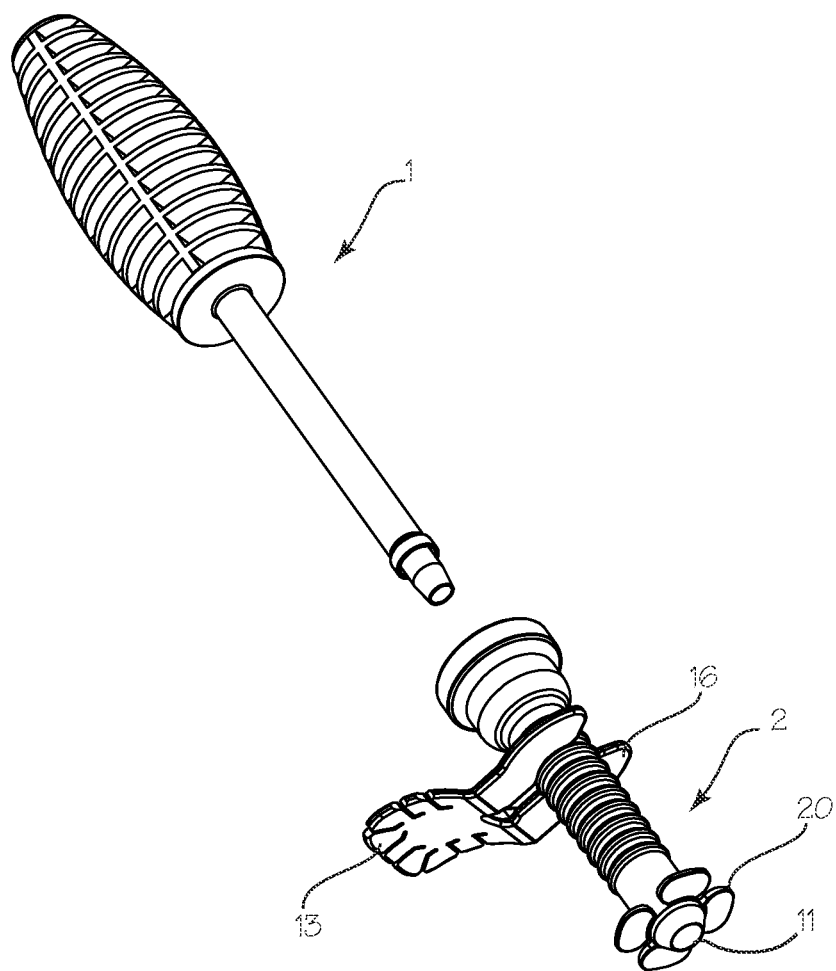
FIGS. 10 through 15 illustrate a cannula with a plurality of flaps disposed on the distal end of the cannula.
Figure 11:
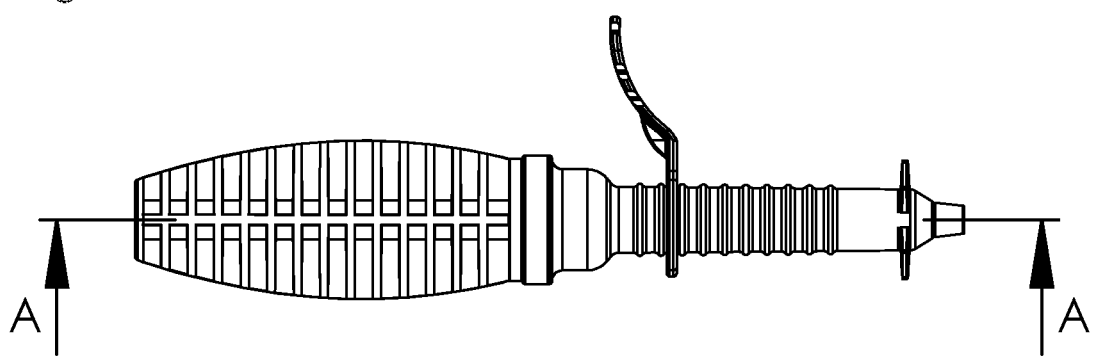
Figure 12:
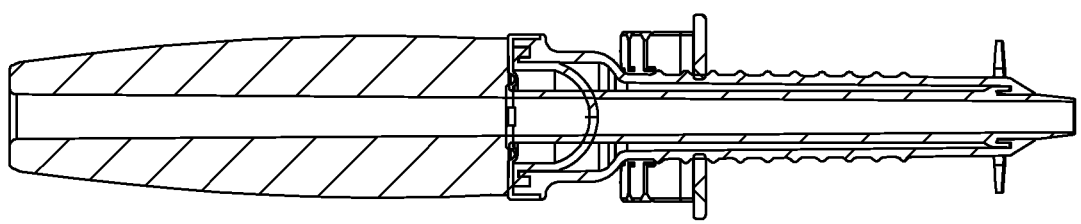
Figure 13:
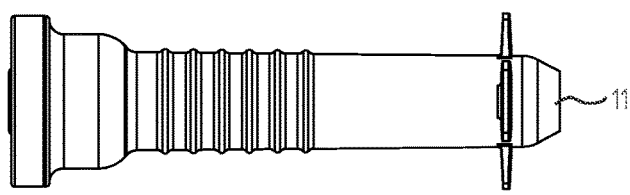
Figure 14:
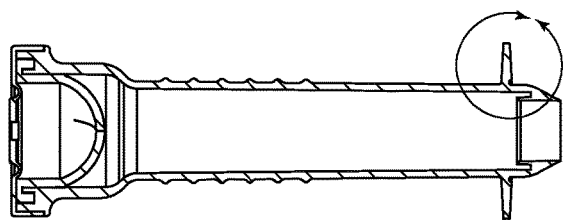
Figure 15:
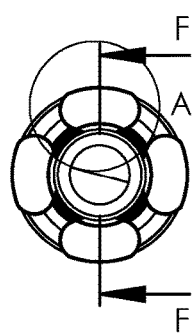

The cannula clip 16 features an extension 13 for sorting sutures. The extension 13 sorts and engages sutures coming out of a shoulder during a rotator cuff repair or any repair procedure involving sutures. The clip 16 has an extension 13 for sorting and arranging sutures for the convenience of the surgeon, consisting of a plurality of slots 19 around the perimeter of the extension 13 of the clip 16. The extension 13 has pairs of slots 19 to sort pairs of sutures used in common double loaded suture anchors, to keep the sutures neatly out of the way of other tools, and conveniently held for retrieval. In this way the surgeon can avoid tying the wrong pairs of sutures together, which can require significant extra surgical time and cost, as well as additional risk and trauma to the patient to correct. These slots 19 may be identified with markings, letters or numbers that associate the location and orientation of the slots to anatomical locations in the joint. An example of such identifying marks is the "clock" nomenclature for identifying anatomic locations on the shoulder glenoid, for example 12:00, 3:00, 6:00, and 9:00. The slots can be tapered to grip different diameters of sutures. The slots can be "L shaped" (as shown in FIG. 10) to cleat the suture and keep the sutures from slipping out of the slot 19.

Figure 16:
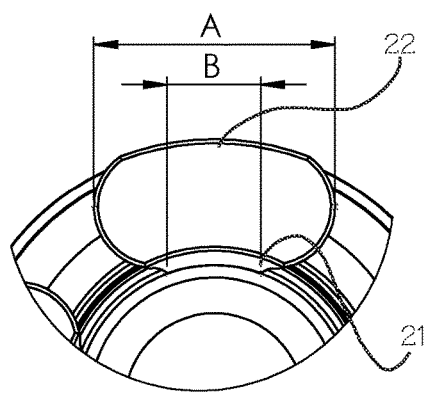
FIGS. 16 and 17 illustrate detailed views of the flaps shown in FIGS. 10 through 15.

FIGS. 10 through 17 illustrates a cannula with a plurality of flaps or tabs 20 which fold back when the cannula is inserted into the incision. Four separate tabs are shown, but any plurality of tabs may be provided. The tabs 20 are disposed at the distal end of the cannula, proximate the distal tip 11, and extend radially outwardly from the outer surface of the cannula. Each tab has a root 21 and a tip 22, with the root 21 at a first end nearest to the cannula outer surface and the tip 22 at the second end of the tab furthest from the cannula outer surface. The root is the part of the flap immediately adjacent to the cannula. As shown in FIG. 16, the root has a width dimension B, that is smaller than the tab face width, dimension A, so that the force of insertion into a portal will cause each tab to fold back.

Figure 17:
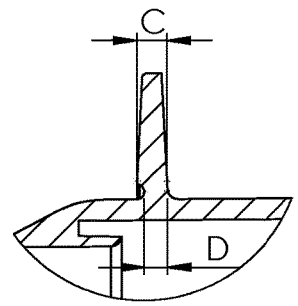

Each flap includes a root portion proximate the outer surface of the cannula, a radially outward portion radially outward of the root, and a proximal face and a distal face, wherein the root portion spans a first circumferential arc (dimension B) and the radially outward portion spans a second circumferential arc (dimension A) larger than the first circumferential arc. The root portion of each flap has a first thickness D, and in the radially outward portion each flap has a second thickness C greater than the first thickness D, as shown in FIG. 17. The tabs are arranged circumferentially around the distal end of the cannula proximate the distal tip. The tabs are made of a flexible material.

Distally positioned flaps or tabs 20 extend radially outwardly from the outer surface of the cannula and are resiliently foldable in a proximal direction while passing through the surgical portal, to lie against the outer surface of the cannula, and resiliently biased to return to a radially outwardly extending position when unconstrained when the distal tip of the cannula is within the arthroscopic workspace.

Figure 18:
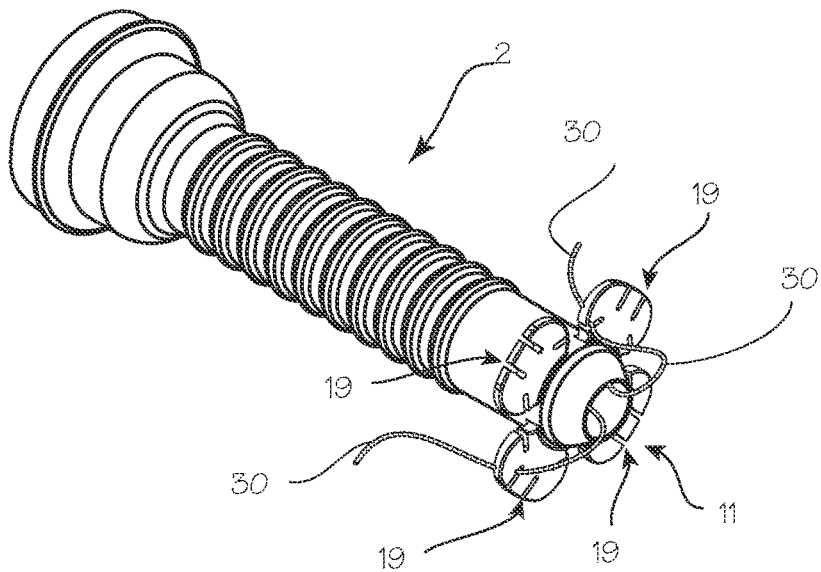
FIG. 18 illustrates a cannula with a plurality of flaps disposed on the distal end of the cannula where the flaps have slots for suture sorting.

FIG. 18 illustrates a cannula with slots 19 disposed on the flaps 20 for sorting and anchoring sutures within the surgical site. A plurality of slots 19 are disposed around the perimeter of the flaps. A slot may also be formed at the root portion of the flaps for suture anchoring and sorting. The slots are configured to accept a segment of suture.

Figure 19:
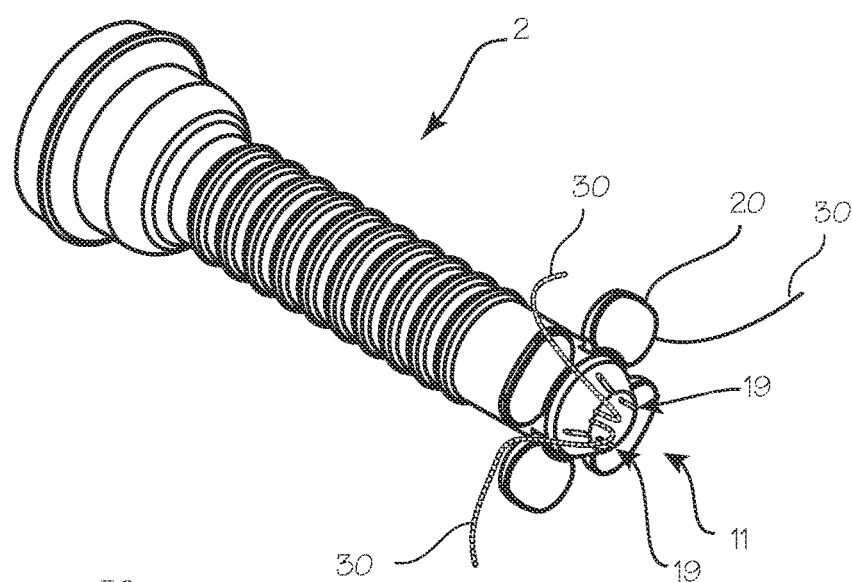
FIG. 19 illustrates a cannula with a plurality of slots in the cannula distal tip.

FIG. 19 illustrates a cannula with slots 19 disposed circumferentially around the cannula distal tip 11 for sorting and anchoring sutures within the surgical site. The slots are configured to accept a segment of suture.

Figure 20:
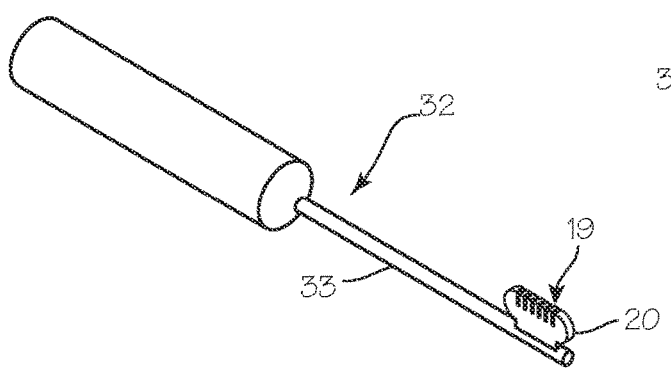
FIG. 20 illustrates a suture sorting accessory.

FIG. 20 illustrates a suture sorting accessory for use in an arthroscopic surgical procedure utilizing sutures. A flexible tab 20 is disposed on the distal end of a handled rigid tube. The flexible tab 20 has slots 19 disposed on the perimeter of the tab. The device may be inserted through a cannula or portal into a surgical site. The slots are configured to accept a segment of suture.

Figure 21:
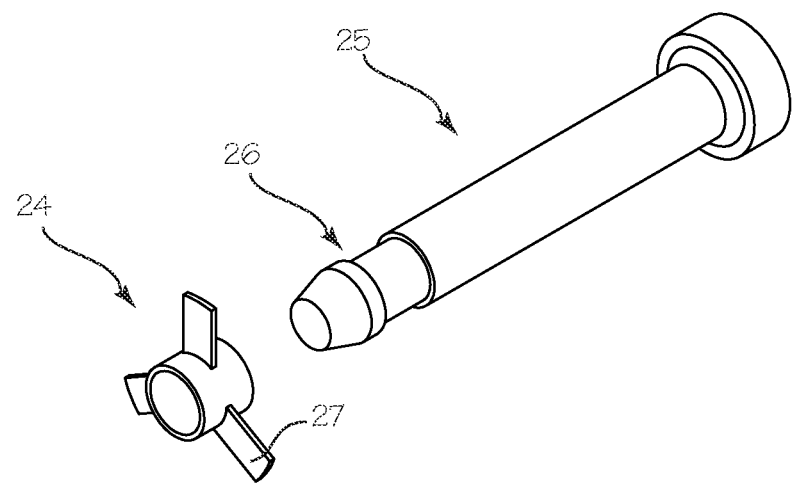
FIGS. 21 and 22 illustrate flaps disposed on a ring configured to engage the tube of the cannula.
Figure 22:
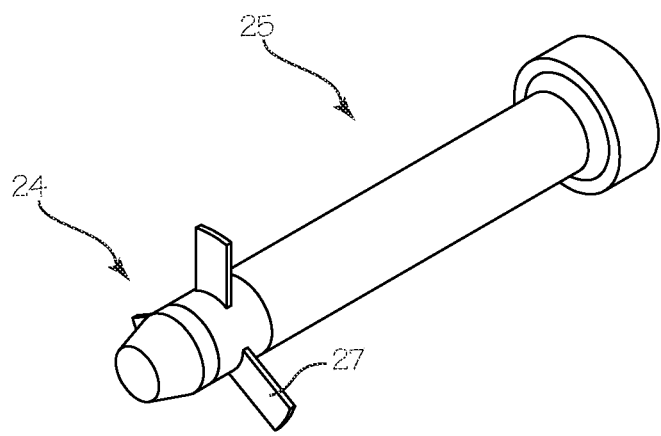

FIGS. 21 and 22 illustrates a cannula where the tabs are disposed on a ring 24 that mounts onto the body of a cannula. The cannula 25 has a retaining groove 26 for matable attachment to a ring 24. The tabs 27 are disposed circumferentially around the ring. The matable attachment of the ring 24 and cannula 25 may be via retaining groove 26, screw, snap-fit or other means.

Figure 23:
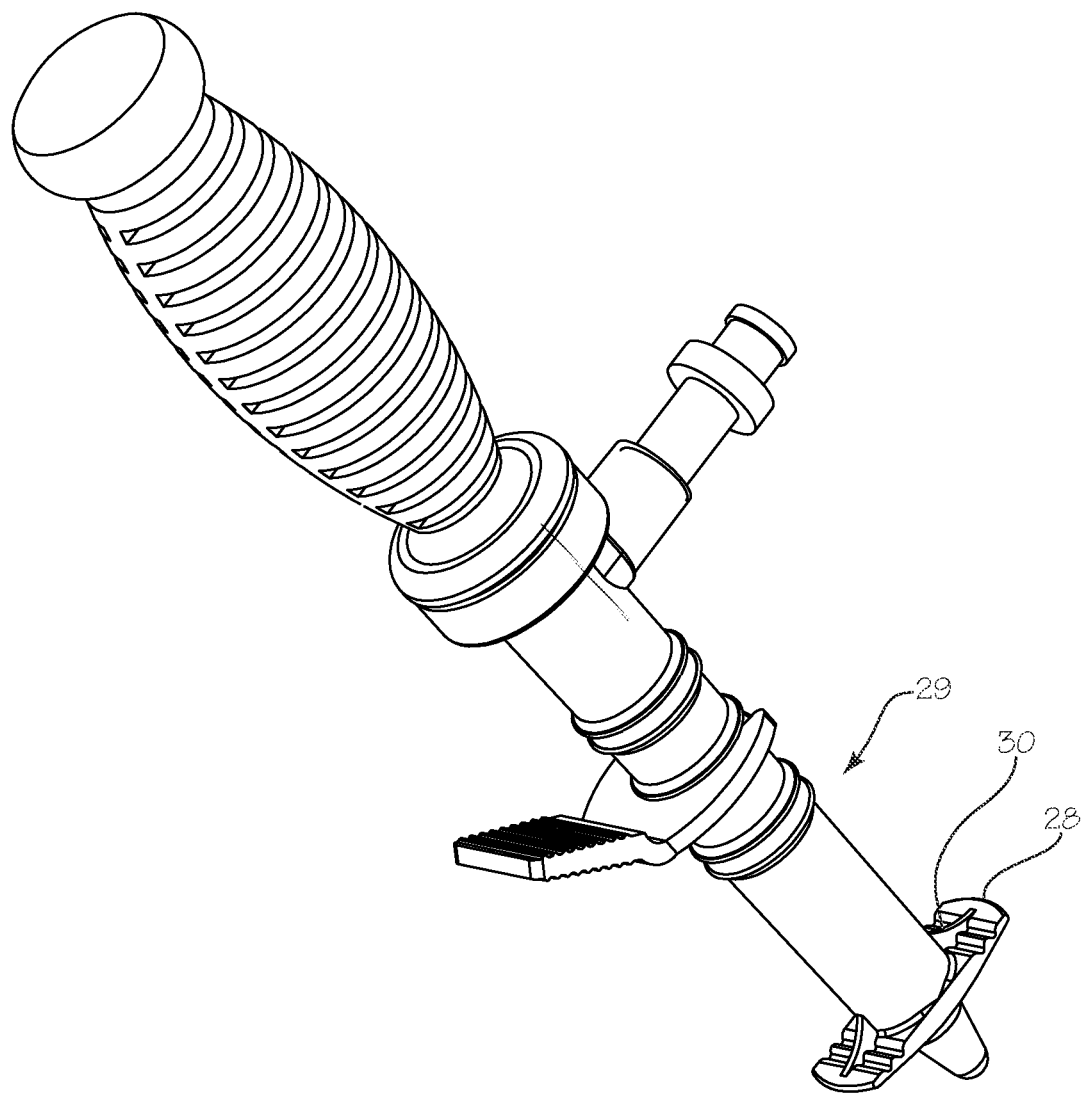
FIG. 23 illustrates a cannula with webs connecting the flaps to the cannula.

FIG. 23 illustrates a cannula with two tabs or flaps 28 disposed on the distal end of the cannula 29 in opposition to each other. Each flap has a proximal face, which is the face closest to the cannula proximal end, and a distal face. Each flap has a flexible web 30 provided on the proximal face of the flap connecting the proximal face of the tab to the outer surface of the cannula. The flaps fold inward toward the outer surface of the cannula when the cannula is being inserted into the incision and resiliently return to the original unconstructed or extended position when the flaps are placed within the arthroscopic workspace. The webs maintain the flaps in the extended position.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method of performing arthroscopic surgery, said method comprising the steps of:
   providing a system for performing arthroscopic surgery, said system comprising:
      an arthroscopic instrument suitable for performing an arthroscopic surgical procedure utilizing sutures;
      a cannula tube, said cannula tube having a proximal end, a distal end, and a lumen extending therethrough, and a distal tip on the distal end, said distal tip configured for insertion through an incision into an arthroscopic workspace, proximate a joint in a patient;
      a plurality of flaps disposed on the distal end of the tube, proximate the distal tip, said flaps extending radially outwardly from an outer surface of the tube, said flaps resiliently foldable in a proximal direction when constrained while passing through the incision, to lie against the outer surface of the tube, and resiliently biased to return to a radially outwardly extending position when unconstrained, wherein each said flap has a perimeter, said flap having at least one slot disposed around the perimeter of the flap, said slot configured to accept a segment of suture;
   anchoring at least one suture within the slot disposed on the perimeter of a flap;
   placing the arthroscopic instrument inside the cannula tube; and
   performing an arthroscopic surgical procedure with the system for performing arthroscopic surgery.

* * * * *